US012616492B2

(12) United States Patent
 Jing et al.

(10) Patent No.: US 12,616,492 B2
(45) Date of Patent: May 5, 2026

(54) THROMBECTOMY DEVICE AND THROMBECTOMY SYSTEM

(71) Applicant: Hangzhou Exceed Medical Technology Co., Ltd, Hangzhou (CN)

(72) Inventors: Hongjuan Jing, Hangzhou (CN); Jiaping Huang, Hangzhou (CN); Changfen Ke, Hangzhou (CN)

(73) Assignee: Hangzhou Exceed Medical Technology Co., Ltd, Hangzhou (CN)

( * ) Notice: Subject to any disclaimer, the term of this patent is extended or adjusted under 35 U.S.C. 154(b) by 194 days.

(21) Appl. No.: 18/529,981

(22) Filed: Dec. 5, 2023

(65) Prior Publication Data

US 2024/0180574 A1     Jun. 6, 2024

(30) Foreign Application Priority Data

Dec. 6, 2022   (CN) .......................... 202211552919.2
Dec. 6, 2022   (CN) .......................... 202211552962.9
Feb. 8, 2023   (CN) .......................... 202310113982.4
Feb. 8, 2023   (CN) .......................... 202310139023.X

(51) Int. Cl.
 *A61B 17/221*         (2006.01)
 *A61B 17/22*          (2006.01)

(52) U.S. Cl.
 CPC .. *A61B 17/221* (2013.01); *A61B 2017/22072* (2013.01)

(58) Field of Classification Search
 CPC ............ A61B 17/221; A61B 17/22031; A61B 17/320725; A61B 2017/00358; A61B 2017/00778; A61B 2017/22035; A61B 2017/22038; A61B 2017/22072; A61B 2017/2212; A61B 2017/2215; A61B 2017/2217
 USPC ......................................... 606/127, 159, 200
 See application file for complete search history.

(56) References Cited

U.S. PATENT DOCUMENTS

2017/0112513 A1* 4/2017 Marchand ............... A61F 2/014
2020/0214728 A1* 7/2020 Follmer ............... A61B 17/221

* cited by examiner

*Primary Examiner* — Kankindi Rwego

(57)          ABSTRACT

Disclosed are a thrombectomy device and a thrombectomy system, where the thrombectomy device includes a thrombectomy net, a pushing tube, and a thrombectomy tube, where the thrombectomy tube is provided with a tube cavity, the thrombectomy net has a radial contraction state and a radial expansion state, and a proximal end of the thrombectomy net is fixedly connected to a distal end of the pushing tube. The thrombectomy device further includes an action tube provided with a first action block and a second action block. A distal end of the thrombectomy net is sleeved on the action tube and slides within a limited range of distance between the first action block and the second action block. When relative displacement against the pushing tube occurs, the thrombectomy net is driven to radially contract or expand. Therefore, the contraction and expansion of the thrombectomy net of the present disclosure are controllable.

10 Claims, 3 Drawing Sheets

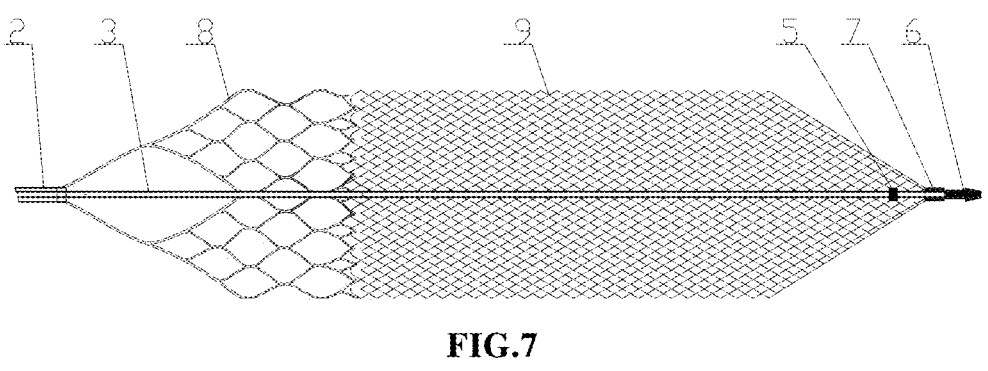
FIG.7
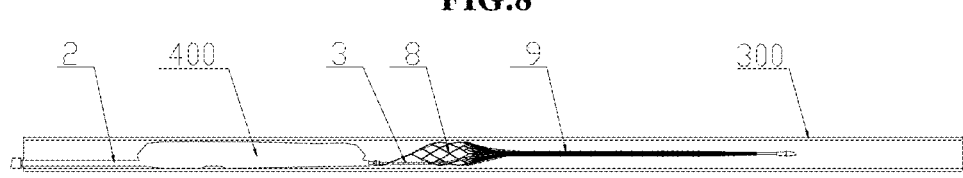
FIG.8
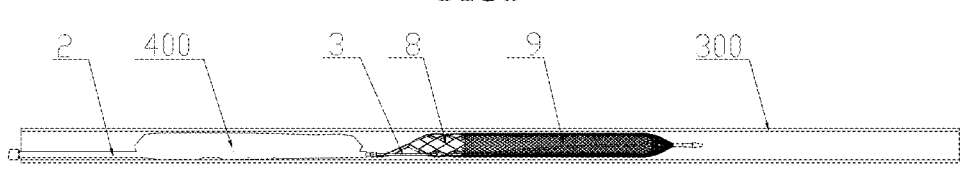
FIG.9
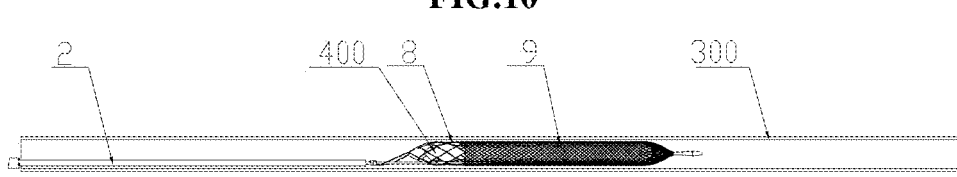
FIG.10
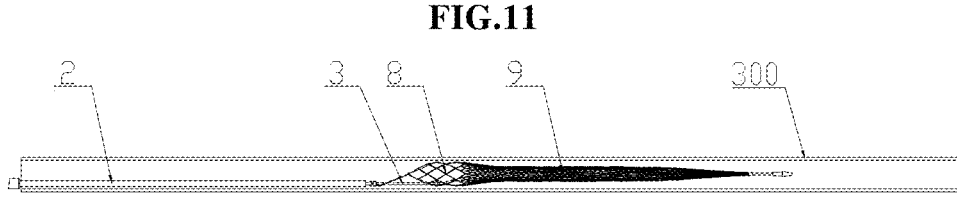
FIG.11
FIG.12
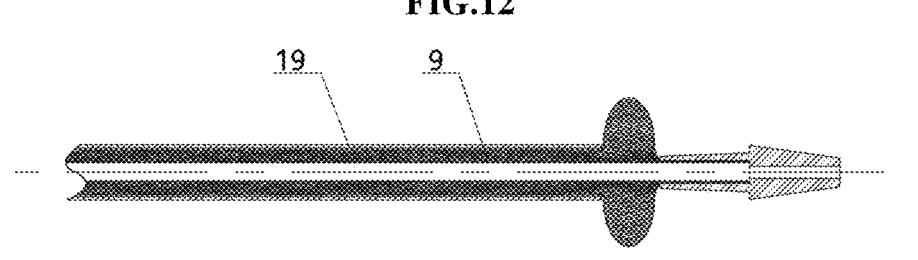
FIG.13

THROMBECTOMY DEVICE AND THROMBECTOMY SYSTEM

CROSS-REFERENCE TO RELATED APPLICATIONS

This application claims priorities from the Chinese patent applications 2022115529629 and 2022115529192 filed Dec. 6, 2022, and from 202310139023X and 2023101139824, filed Feb. 8, 2023, the content of which are incorporated herein in the entirety by reference.

TECHNICAL FIELD

The present disclosure relates to the technical field of medical devices, and particularly relates to a thrombectomy device and a thrombectomy system.

BACKGROUND

Mechanical thrombectomy is a process of conveying a thrombectomy device to a lesion site to capture the thrombus and ultimately take the thrombus out of a human body. Existing mechanical thrombectomy means generally include direct thrombectomy, thrombus fragmentation by laser, and thrombectomy through a capture device, where the direct thrombectomy achieves more thorough thrombectomy, but causes excessive damage to vascular walls and easily leads to various concurrent inflammations. In contrast, the thrombus fragmentation by laser is very difficult, because too low laser energy will cause failure of operation, while too high energy might damage blood vessels, easily causing various complications. Therefore, currently the capture device is most commonly used for thrombectomy.

The capture device is used to achieve thrombectomy through a thrombectomy net with automatic expansion properties. For example, a Chinese patent CN104068911A discloses a vascular thrombectomy apparatus and a thrombectomy device, as well as a specific process of thrombectomy as follows: conveying the thrombectomy net to a lesion site in a blood vessel, releasing the thrombectomy net, locating the thrombectomy net through a developing marker, gradually expanding by means of an elastic force of the thrombectomy net to make the thrombectomy net attached to the vascular wall, withdrawing the thrombectomy net to capture the thrombus, and finally taking the thrombectomy net out of the body of a patient to complete the thrombectomy. The thrombectomy device disclosed in the patent CN104068911A fully utilizes the thrombectomy net with automatic expansion properties to achieve its contraction and expansion. However, when a blood vessel has complex lesions, such as existence of a superhard thrombosis, the thrombectomy net maybe is not capable to expand smoothly, which might result in that the thrombectomy device cannot be "opened", thus further leading to failure or a poor effect of thrombectomy.

SUMMARY

In view of the above defects in the prior art, the present disclosure provides a thrombectomy device and a thrombectomy system to solve the technical problem.

The present disclosure provides a thrombectomy device, and the thrombectomy device includes a thrombectomy net, a pushing tube, and a thrombectomy tube, where the thrombectomy tube is provided with a tube cavity that accommodates the thrombectomy net and the pushing tube, the thrombectomy net has a radial contraction state and a radial expansion state, and a proximal end of the thrombectomy net is fixedly connected to a distal end of the pushing tube. The thrombectomy device further includes an action tube provided with a first action block and a second action block, where the first action block and the second action block are both fixed on the action tube and spaced apart from each other. A distal end of the thrombectomy net is sleeved on the action tube and is capable to slide within a limited range of distance between the first action block and the second action block. When relative displacement against the pushing tube occurs after the action tube is configured to move in a predetermined direction, the thrombectomy net is driven to radially contract by means of the first action block or to radially expand by means of the second action block. The thrombectomy net includes a first thrombectomy subnet and a second thrombectomy subnet. An action structure is arranged between the action tube and the first thrombectomy subnet, and the action structure is configured to drive the first thrombectomy subnet to shorten and expand radially, when the action tube, by means of the second action block, drives a distal end of the second thrombectomy subnet to slide towards a proximal end thereof so as to make the second thrombectomy subnet expand radially.

Further, the proximal end of the first thrombectomy subnet is an open end and fixedly connected to the distal end of the pushing tube, the distal end of the first thrombectomy subnet and the proximal end of the second thrombectomy subnet are both open ends and connected in a smooth transition manner, and the distal end of the second thrombectomy subnet is fixedly connected to a sliding block and converged at the sliding block to form a retraction end, where the sliding block is sleeved on the action tube and configured to slide within a limited range of distance between the first action block and the second action block.

Further, the first thrombectomy subnet is a cutting stent configured for separating a thrombus from a blood vessel by cutting the thrombus therein, and the second thrombectomy subnet is a braided stent configured for collecting the thrombus separated out.

Further, the first action block is located inside the second thrombectomy subnet and protrudes from an outer surface of the action tube, and after the first action block abuts against the distal end of the second thrombectomy subnet, at least part of the distal end of the second thrombectomy subnet is stretched.

Further, the second action block is located outside the second thrombectomy subnet, and the distal end of the second action block is formed as a tapered end.

Further, the action tube and the pushing tube are coaxially arranged, and at least a portion of the action tube is located inside the pushing tube.

Further, the action structure includes a first action end fixed on the action tube and a second action end fixed on the first thrombectomy subnet, and the action tube abuts against the second action end through the first action end to drive the first thrombectomy subnet to shorten.

Further, the first action end is an action convex protruding from the outer surface of the action tube, the second action end is an action ring sleeved on the action tube, and a maximum radial size of the action ring is smaller than the maximum radial size of the action convex.

The present disclosure further provides a thrombectomy system, and the thrombectomy system includes a thrombus trapping device and the above thrombectomy device, where the thrombus trapping device includes a sheath tube, a trapping tube and a trapping net that can be stored in the sheath tube. The trapping net is connected to the trapping tube, the pushing tube is configured to push the thrombectomy net into the blood vessel for thrombectomy and to withdraw the thrombectomy net with an embedded thrombus back into the sheath tube, and the trapping net is configured to at least partially wrap the thrombectomy net in the process that the thrombectomy net with the embedded thrombus is withdrawn back into the sheath tube.

Further, after completion of the thrombectomy through the thrombectomy net and before the trapping net wraps at least part of the thrombectomy net, the entire thrombectomy net is in a contracted state at least in a stage, and the trapping net is turned over from inside to outside to form an outward flipping state, with an inward flipping guide surface.

Further, the inward flipping guide surface is a tapered arc surface.

Further, when the trapping tube and the pushing tube are moved synchronously from the distal end to the proximal end, exposed inside of the trapping net is quickly flipped inward along the inward flipping guide surface to at least partially wrap the thrombectomy net, and is withdrawn back into the sheath tube together with the thrombectomy net.

Further, the trapping net is provided with a first open end and a second open end that are axially opposite to each other, where the inward flipping guide surface is formed at a location near the first open end of the trapping net, before the trapping net wraps at least part of the thrombectomy net, the first open end is flipped inward and relatively fixedly connected to a distal end of the trapping tube to form the distal end of the trapping net, and the second open end is a free end and is formed as a proximal end of the trapping net.

Further, when the trapping tube and the pushing tube are moved synchronously from the distal end to the proximal end, the sheath tube abuts against the trapping net to make the trapping net flip inward; and after the trapping net is flipped inward in place, the first open end is formed as the proximal end of the trapping net, and the second open end is formed as the distal end of the trapping net.

Further, the trapping net has a radial contraction state and a radial expansion state, where the trapping net located inside the sheath tube is in a contracted state, the trapping net located outside the sheath tube is in an expansion state, and the radial size of the trapping net in the expansion state is greater than the radial size of the sheath tube.

Compared with prior art, the action tube of the present disclosure is provided with the first action block and the second action block spaced apart from each other, where the first action block and the second action block drive the thrombectomy net to radially contract and expand in a controllable manner, which not only prevents the problem that the thrombectomy net cannot be contracted and smoothly taken out of the blood vessel after thrombectomy, but also prevents the problem that the thrombectomy net cannot be expanded and attached to an inner wall of the blood vessel, which results in failure of complete thrombectomy; further, after the contraction of the thrombectomy net, the distal end of the thrombectomy net is also capable to move towards the second action block relative to the action tube for the purpose of further contraction, and after the expansion of the thrombectomy net, the distal end of the thrombectomy net is also capable to move towards the first action block relative to the action tube for the purpose of further expansion; and therefore, the distal end of the thrombectomy net is not completely limited and will be dynamically adjusted with changes in the volume of a thrombus within the thrombectomy net and other conditions, thereby facilitating the automatic position adjustment and uniform distribution of thrombi within the thrombectomy net, so that the thrombectomy effect is improved.

BRIEF DESCRIPTION OF THE DRAWINGS

With reference to accompanying drawings and a detailed description below, the present disclosure and its accompanying advantages and features will be understood in an easier and more complete manner.

FIG. 7 is a schematic diagram of an unfolded structure of the thrombectomy net and the pushing tube in FIG. 2.

FIGS. 8-12 are schematic diagrams of a process of thrombectomy through the thrombectomy device.

FIG. 13 is a schematic diagram of a "bulge" that occurs during thrombectomy in the prior art.

Figures 1, 2, 3, 4, 5, 6:
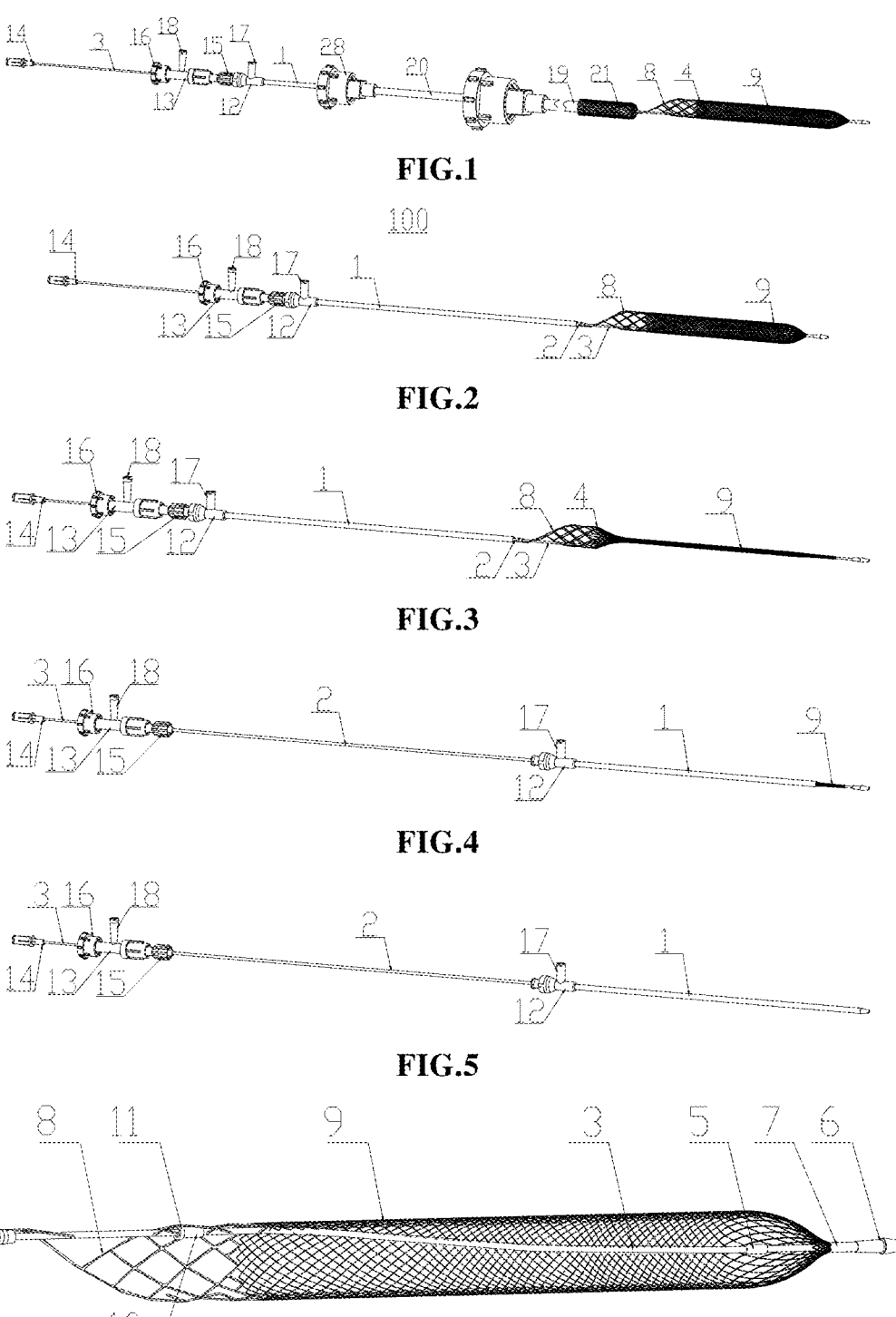
FIG. 1 is a schematic diagram of a structure of a thrombectomy system.
FIG. 2 is a schematic diagram of a structure of a thrombectomy device in FIG. 1 (a thrombectomy net is in an expansion state and located outside a thrombectomy tube).
FIG. 3 is a schematic diagram of a structure of the thrombectomy device with the thrombectomy net in a contracted state and located outside the thrombectomy tube.
FIG. 4 is a schematic diagram of a structure of the thrombectomy device with the thrombectomy net in the contracted state and partially located inside the thrombectomy tube.
FIG. 5 is a schematic diagram of a structure of the thrombectomy device with the thrombectomy net in the contracted state and completely located inside the thrombectomy tube.
FIG. 6 is a schematic diagram of a three-dimensional structure of the thrombectomy net and a pushing tube in FIG. 2.

In the figures: 1. thrombectomy tube, 2. pushing tube, 3. action tube, 4. thrombectomy net, 5. first action block, 6. second action block, 7. sliding block, 8. first thrombectomy subnet, 9. second thrombectomy subnet, 10. first action end, 11. second action end, 12. first tube base, 13. second tube base, 14. third tube base, 15. first connector, 16. second connector, 17. first injection pipe, 18. second injection pipe, 19. sheath tube, 20. trapping tube, 21. trapping net, 22. first open end, 23. second open end, 24. inward flipping guide surface, 25. outer layer, 26. elastic net, 27. inner layer, 28. trapping tube base; 100. thrombectomy device, 200. thrombus trapping device, 300. blood vessel, and 400. thrombus.

It should be noted that the accompanying drawings are intended to illustrate the present disclosure, but not to limit the present disclosure. It should be noted that the accompanying drawings showing structures maybe are not drawn to scale. In the accompanying drawings, the same or similar elements are marked with the same or similar symbols.

DETAILED DESCRIPTION OF THE EMBODIMENTS

In order to make the content of the present disclosure clearer and easier to understand, a detailed description will be made below with reference to some specific embodiments and accompanying drawings.

A "proximal end" and a "distal end" referred to in the present disclosure should be understood as those observed from a direction of an attending doctor, where the "proximal end" refers to an end close to the attending doctor, and corresponds to a "left end" referred to in the accompanying drawings, while the "distal end" refers to an end away from the attending doctor, and corresponds to a "right end" referred to in the accompanying drawings.

As shown in FIGS. 1-19, a thrombectomy system of this embodiment includes a thrombectomy device 100 and a thrombus trapping device 200, where the thrombectomy device 100 is configured for thrombectomy in a blood vessel, and the thrombus trapping device 200 is configured to wrap the thrombectomy device 100 after the thrombectomy through the thrombectomy device 100 is completed and before the thrombectomy device 100 is taken out of the blood vessel, in order to prevent the thrombi in the thrombectomy device 100 from escaping so as to avoid failure or a poor effect of the thrombectomy.

A structure of the thrombectomy device 100 includes a thrombectomy tube 1, a pushing tube 2, an action tube 3, and a thrombectomy net 4, where the thrombectomy tube 1 is provided with a tube cavity that accommodates the pushing tube 2 and the thrombectomy net 4, the pushing tube 2 and the action tube 3 are both hollow tubes to facilitate passage of pusher guide wires, the action tube 3 is at least partially and slidably arranged in the pushing tube 2, that is, the thrombectomy tube 1, the pushing tube 2, and the action tube 3 are arranged coaxially from outside to inside, and the thrombectomy net 4 is a self-expanding net with a plurality of net holes, so that the thrombectomy net 4 has a radial contraction state and a radial expansion state; the proximal end and the distal end of the thrombectomy net 4 are an open end and a retraction end respectively; when the thrombectomy net 4 is located inside the blood vessel and moves relative to the blood vessel from the distal end to the proximal end, so that the thrombus inside the blood vessel can be cut, separated and collected in succession; and the proximal end of the thrombectomy net 4 is fixedly connected to the distal end of the pushing tube 2, so that the pushing tube 2 is capable to push the thrombectomy net 4 into the blood vessel, withdraw back the thrombectomy net 4 for thrombectomy, and withdraw the thrombectomy net 4 with an embedded thrombus back into thrombus trapping device 200 to complete thrombectomy.

An action tube 3 is provided with a first action block 5 and a second action block 6, where the first action block 5 and the second action block 6 are both fixed on the action tube 3 and spaced apart from each other. A distal end of the thrombectomy net 4 is sleeved on the action tube 3 and is capable to slide within a limited range of distance between the first action block 5 and the second action block 6. When relative displacement against the pushing tube 2 occurs after the action tube 3 is configured to move in a predetermined direction, the thrombectomy net 4 is driven to radially contract by means of the first action block 5 or to radially expand by means of the second action block 6. Compared with prior art, the thrombectomy net 4 of the present disclosure solely relies on its own expansion properties to achieve retraction and expansion. This embodiment not only prevents the problem that the thrombectomy net 4 cannot be contracted and smoothly taken out of the blood vessel after thrombectomy, but also prevents the problem that the thrombectomy net 4 cannot be expanded and attached to an inner wall of the blood vessel, which results in failure of complete thrombectomy; further, after the contraction of the thrombectomy net 4, the distal end of the thrombectomy net 4 is also capable to move towards the second action block 6 relative to the action tube 3 for the purpose of further contraction, and after the expansion of the thrombectomy net 4, the distal end of the thrombectomy net 4 is also capable to move towards the first action block 5 relative to the action tube 3 for the purpose of further expansion; and therefore, the distal end of the thrombectomy net 4 is not completely limited and will be dynamically adjusted with changes in the volume of a thrombus within the thrombectomy net 4 and other conditions, thereby facilitating the automatic position adjustment and uniform distribution of thrombi within the thrombectomy net 4, so that the thrombectomy effect of this embodiment is improved.

The distal end of the thrombectomy net 4 is fixedly connected to a sliding block 7 and converged at the sliding block 7 to form a retraction end, where the sliding block 7 is sleeved on the action tube 3 and configured to slide within a limited range of distance between the first action block 5 and the second action block 6 and rotate in a direction relative to the action tube 3. The first action block 5 is located inside the thrombectomy net 4, and the second action block 6 is located outside the thrombectomy net 4. When relative displacement against the pushing tube 2 occurs after the action tube 3 is pushed from the proximal end to the distal end, the pushing tube 3, by means of the first action block 5, is capable to drive the sliding block 7 to slide towards the distal end direction so that the thrombectomy net 4 extends to contract radially. When the relative displacement against the pushing tube 2 occurs after the action tube 3 is pulled from the distal end to the proximal end, the action tube 3, by means of the second action block 6, is capable to drive the sliding block 7 to slide towards the proximal end direction so that the thrombectomy net 4 is shortened to expand radially.

The first action block 5 is an annular boss protruding from an outer surface of the action tube 3, and the annular boss is fixedly connected with a split of the action tube 3. Further, the first action block 5 plays a role of supporting the thrombectomy net 4, and ensures that the thrombectomy net 4 in a radial contraction state has a certain thrombus storage space, thus avoiding the problem that incomplete thrombectomy occurs after the thrombus in the thrombectomy net 4 is squeezed out of and escapes from a too small thrombus storage space. Specifically, when preset relative displacement against the pushing tube 2 occurs after the action tube 3 moves from the proximal end to the distal end, the first action block 5 moves to the distal end of the thrombectomy net 4 to abut against and at least partially stretch the distal end of the thrombectomy net 4. Moreover, since the first action block 5 is arranged to protrude from the outer surface of the action tube 3, the first action block 5 is capable to aggregate some thrombi inside the thrombectomy net 4, thus effectively preventing the thrombi at the distal end of the thrombectomy net 4 from moving to the proximal end, so that efficiency of thrombectomy at the proximal end is ensured. The second action block 6 is also an annular boss protruding from the outer surface of the action tube 3, the distal end of the second action block 6 is formed as a tapered end to penetrate the thrombus easily, and after the thrombectomy net 4 is stored in the tube cavity of the thrombectomy tube 1, the second action block 6 is clamped at the distal end of the thrombectomy tube 1.

The radial contraction and expansion of the thrombectomy net 4 in this embodiment can be achieved by controlling the action tube 3. After completion of the thrombectomy through the thrombectomy net 4 and before the thrombectomy net 4 is completely withdrawn back into a sheath tube, the entire thrombectomy net 4 is configured to be in a contracted state at least in a stage, that is, the entire thrombectomy net 4 must be in a radial contraction state before it is fully withdrawn back into the sheath tube, so that at the time of thrombectomy, the thrombectomy net 4 is in a radial expansion state to separate and aggregate the thrombi in the blood vessel, and after completion of the thrombectomy, the thrombectomy net 4 is in a contracted state to reduce a radial size thereof, which makes it easier to withdraw the thrombectomy net 4 with an embedded thrombus back into the thrombus trapping device 200 to remove the thrombus from the blood vessel. Moreover, during the radial contraction of the entire thrombectomy net 4, the thrombus in the thrombectomy net 4 is radially compressed and subjected to axial displacement, ultimately resulting in that distribution of the thrombi in the thrombectomy net 4 is relatively uniform, so that the radial size thereof will not be enlarged due to aggregation of a large amount of thrombi at a certain location of the thrombectomy net 4, and the thrombus will not be squeezed out of and escape due to collision between the thrombectomy net 4 and the thrombus trapping device 200.

The thrombectomy net 4 includes a first thrombectomy subnet 8 and a second thrombectomy subnet 9, where the first thrombectomy subnet 8 and the second thrombectomy subnet 9 are both self-expanding nets with a plurality of net holes, so that both the first thrombectomy subnet 8 and the second thrombectomy subnet 9 have the radial contraction state and the radial expansion state. The first thrombectomy subnet 8 is a cutting stent that may be made by cutting a self-expanding tube with laser, and compared to a braided stent, the cutting stent is harder, has a low shrinkage rate (i.e., less deformation), and is suitable for cutting the thrombi in the blood vessel to separate them from the blood vessel. The second thrombectomy subnet 9 is a braided stent that may be made by weaving self-expanding wires, and the braided stent is relatively soft, has a high shrinkage rate (i.e., large deformation) and smaller net holes, and is suitable for collecting the thrombi separated out. The proximal end and the distal end of the first thrombectomy subnet 8 are both open ends, the proximal end of the second thrombectomy subnet 9 is an open end, the distal end of the second thrombectomy subnet 9 is fixedly connected to the sliding block 7 to form the retraction end, the proximal end of the first thrombectomy subnet 8 is fixedly connected to the distal end of the pushing tube 2, the distal end of the first thrombectomy subnet 8 is fixedly connected to the proximal end of the second thrombectomy subnet 9 with a smooth transition connection at a joint therebetween, and the second thrombectomy subnet 9 is configured to collect the thrombi separated out. When the first thrombectomy subnet 8 and the second thrombectomy subnet 9 are withdrawn back, the thrombi in the blood vessel are collected in the second thrombectomy subnet 9 after penetrating an opening of the proximal end of the first thrombectomy subnet 8.

The first action block 5 is located inside the second thrombectomy subnet 9, and the second action block 6 is located outside the second thrombectomy subnet 9. Because the sliding block 7 is fixed at the distal end of the second thrombectomy subnet 9, when relative displacement against the pushing tube 2 occurs after the action tube 3 moves from the distal end to the proximal end, the action tube 3, by means of the second action block 6 and the sliding block 7, directly acts on the distal end of the second thrombectomy subnet 9 to drive the second thrombectomy subnet 9 to move towards the proximal end thereof, directly resulting in that the second thrombectomy subnet 9 is shortened to expand radially, and drives the first thrombectomy subnet 8 connected to it to expand radially after being indirectly shortened, that is, the action tube 3 does not directly make the first thrombectomy subnet 8 shorten to expand radially. If the second thrombectomy subnet 9 is longer, the first thrombectomy subnet 8 cannot be fully expanded, that is, an expansion effect is not ideal, which will affect the effect of cutting and separating the thrombi by means of the first thrombectomy subnet 8. Therefore, in this embodiment, an action structure is arranged between the action tube 3 and the first thrombectomy subnet 8, and the action structure is configured to directly drive the first thrombectomy subnet 8 shorten to expand radially, when the action tube 3, by means of the second action block 6, drives the distal end of the second thrombectomy subnet 9 to slide towards the proximal end thereof so as to make the second thrombectomy subnet 9 expand radially, which directly drives the second thrombectomy subnet 9 and the first thrombectomy subnet 8 to expand, thus greatly improving the thrombectomy effect. The action structure includes a first action end 10 fixed on the action tube 3 and a second action end 11 fixed on an inner wall of the first thrombectomy subnet 8, where the first action end 10 is an action convex protruding from the outer surface of the action tube 3, and the second action end 11 is an action ring protruding towards an inner surface of the first thrombectomy subnet 8 and sleeved on the action tube 3. A maximum radial size of the action ring is smaller than the maximum radial size of the action convex, so that the action tube 3, by means of the first action end 10, abuts against the second action end 11 and directly drives the first thrombectomy subnet 8 to shorten and expand radially.

The proximal end of the thrombectomy tube 1 is fixedly sleeved with a first tube base 12, the first tube base 12 is communicated with the tube cavity of the thrombectomy tube 1, the proximal end of the pushing tube 2 penetrates through the first tube base 12 and is fixedly sleeved with a second tube base 13, the second tube base 13 is communicated with inside of the pushing tube 2, the proximal end of the action tube 3 penetrates through the second tube base 13 and is fixedly sleeved with a third tube base 14, and the third tube base 14 is communicated with inside of the action tube 3. The distal end of the second tube base 13 is provided with a first connector 15 that can be relatively fixedly connected to the first tube base 12. For example, the first connector 15 is fixedly connected to the distal end of the second tube base 13 and can be fixed to the first tube base 12 in an inserted or a clamped manner, or the first connector 15 is rotatably connected to the distal end of the second tube base 13 and can be rotationally fixed to the first tube base 12. The proximal end of the second tube base 13 is provided with a second connector 16 that is capable to relatively fixedly connect the third tube base 14 to the action tube 3. For example, the second connector 16 is rotatably connected to the proximal end of the second tube base 13, and when the second connector 16 is rotated, a clamping sleeve with clamping holes inside the second tube base 13 is driven to deform so as to lock the action tube 3, so that relative fixation between the action tube 3 and the third tube base 14 is achieved.

Referring to FIG. 8, in an actual process of thrombectomy through the thrombectomy device 100, firstly, the thrombectomy tube 1 containing the first thrombectomy subnet 8 and the second thrombectomy subnet 9 is conveyed into a blood vessel 300, and by means of the pusher guide wire and the tapered end at the distal end of the second action block 6, the thrombectomy tube 1 penetrates through the distal end of a thrombus 400 in the blood vessel 300; next, the thrombectomy tube 1 is pulled from the distal end to the proximal end to withdraw back the thrombectomy tube 1, so that the first thrombectomy subnet 8 and the second thrombectomy subnet 9 are in a released state, at this time, because the first action block 5 abuts against or approaches the distal end of the second thrombectomy subnet 9, the first thrombectomy subnet 8 and the second thrombectomy subnet 9 are still in a contracted state as shown in FIG. 9, moreover, the proximal end of the first thrombectomy subnet 8 is located at the distal end of the thrombus 400, and the first tube base 12 is connected to the first connector 15 for fixing, such that the thrombectomy tube 1 and the pushing tube 2 are relatively fixed; then, the action tube 3 is pulled from the distal end to the proximal end until the preset displacement of the action tube 3 relative to the pushing tube 2 occurs, so that the action tube 3, by means of the second action block 6 and the sliding block 7, directly acts on the distal end of the second thrombectomy subnet 9 to drive the second thrombectomy subnet 9 to move towards the proximal end thereof, directly resulting in that the second thrombectomy subnet 9 is shortened to expand radially, and drives the first thrombectomy subnet 8 connected to it to expand radially after being indirectly shortened, meanwhile the action tube 3, by means of the first action end 10, abuts against the second action end 11 and directly drives the first thrombectomy subnet 8 to shorten and expand radially, and after being put in place, the action tube 3 is relatively fixed to the pushing tube 2 by means of the second connector 16, and the expansion state shown in FIG. 10 of the first thrombectomy subnet 8 and the second thrombectomy subnet 9 is ultimately achieved; then, any one of the thrombectomy tube 1, the pushing tube 2 and the action tube 3 is pulled from the distal end to the proximal end to drive the first thrombectomy subnet 8 and the second thrombectomy subnet 9 to move in a direction relative to the blood vessel 300, during the process, the first thrombectomy subnet 8 cuts the thrombus 400 inside the blood vessel 300 to separate it from the blood vessel 300, and the second thrombectomy subnet 9 collects the thrombus 400 separated out, that is, the thrombus 400 inside the blood vessel 300 is collected in the second thrombectomy subnet 9 after penetrating an opening of the proximal end of the first thrombectomy subnet 8, and finally the thrombus 400 is located within the first thrombectomy subnet 8 and the second thrombectomy subnet 9, as shown in FIG. 11; finally, any one of the thrombectomy tube 1, the pushing tube 2 and the action tube 3 is further pulled from the distal end to the proximal end, so that the first thrombectomy subnet 8 and the second thrombectomy subnet 9 move into the thrombus trapping device 200 in a direction relative to the blood vessel 300 to withdraw them from the blood vessel 300, in order to facilitate the smooth withdrawal of the first thrombectomy subnet 8 and the second thrombectomy subnet 9 with the embedded thrombus 400 back into thrombus trapping device 200, the proximal end of the first thrombectomy subnet 8 is configured to be an inclined opening, just after the proximal end of the first thrombectomy subnet 8 enters the thrombus trapping device 200, the action tube 3 and the pushing tube 2 are unlocked by means of the second connector 16, and the action tube 3 is pushed from the proximal end to the distal end until the preset relative displacement against the pushing tube 2 occurs after the action tube 3 moves from the proximal end to the distal end, so that the action tube 3, by means of the first action block 5 and the sliding block 7, directly acts on the distal end of the second thrombectomy subnet 9 to drive the second thrombectomy subnet 9 to move towards the distal end thereof, directly resulting in that the second thrombectomy subnet 9 is extended to contract radially, and drives the first thrombectomy subnet 8 connected to it to contract radially after being indirectly extended, as shown in FIG. 12, that is, before being completely withdrawn back into the thrombus trapping device 200, the first thrombectomy subnet 8 and the second thrombectomy subnet 9 are configured to be in a contracted state overall at least in a stage, that is, the first thrombectomy subnet 8 and the second thrombectomy subnet 9 with the embedded thrombus 400 must be in a radial contraction state overall before they are fully withdrawn back into the thrombus trapping device 200, in order to avoid the situation that the thrombus 400 is squeezed out of and escapes due to collision between the first thrombectomy subnet 8/the second thrombectomy subnet 9 and the inner wall of the thrombus trapping device 200.

Moreover, the distal end of the second thrombectomy subnet 9, namely the sliding block 7, is sleeved on the action tube 3 and is capable to slide within the limited range of distance between the first action block 5 and the second action block 6, so it is not completely restricted, such that after the first thrombectomy subnet 8 and the second thrombectomy subnet 9 contract, the distal end of the second thrombectomy subnet 9 is still capable to move towards the second action block 6 relative to the action tube 3 to further contract, thus avoiding the situation that the second thrombectomy subnet 9 cannot be smoothly withdrawn back into a sheath tube 19 of the thrombus trapping device 200 due to "bulging" as shown in FIG. 13. At the same time, after the expansion of the first thrombectomy subnet 8 and the second thrombectomy subnet 9, the distal end of the second thrombectomy subnet 9 is also capable to move towards the first action block 5 relative to the action tube 3 for the purpose of further expansion. Therefore, such arrangement results in that the first thrombectomy subnet 8 and the second thrombectomy subnet 9 can be dynamically adjusted with changes in the volume of thrombi therein and other conditions, thereby facilitating the automatic position adjustment and uniform distribution of the thrombus 400 in the first thrombectomy subnet 8 and the second thrombectomy subnet 9, so that a good thrombectomy effect is achieved.

The first tube base 12 is provided with a first injection pipe 17, and the second tube base 13 is provided with a second injection pipe 18, where the first injection pipe 17 and the second injection pipe 18 are configured for injecting physiological saline, contrast agents, etc., the first injection pipe 17 is communicated with the tube cavity of the thrombectomy tube 1 to connect a space formed between the inner wall of the thrombectomy tube 1 and the outer wall of the pushing tube 2, and the second injection pipe 18 is communicated with the inside of the pushing tube 2 to connect a space formed between the inner wall of pushing tube 2 and the outer wall of the action tube 3.

Figure 14:
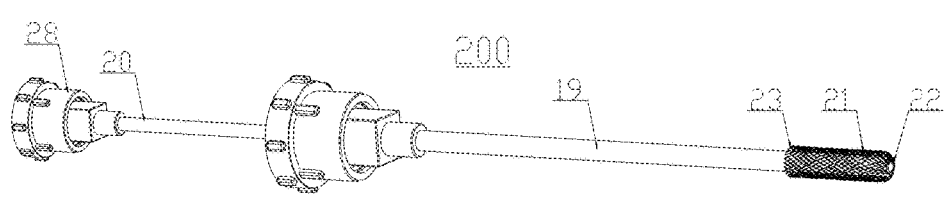
FIG. 14 is a schematic diagram of a structure of a thrombus trapping device in FIG. 1 (a trapping net is located outside a trapping tube and sleeved on a sheath tube).
Figure 15:
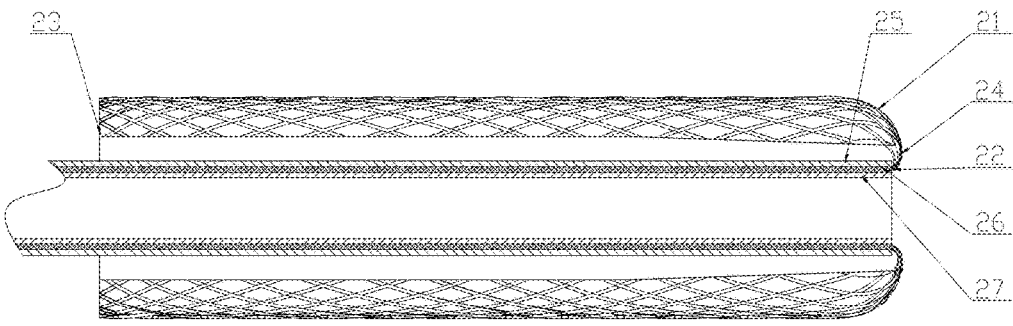
FIG. 15 is a partial sectional view of the trapping net and trapping tube in FIG. 14.
Figure 16:
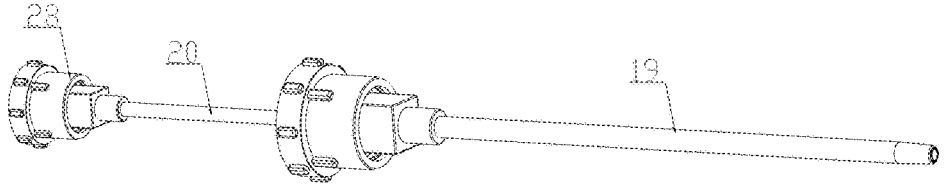
FIG. 16 is a schematic diagram of a structure of the thrombus trapping device of the trapping net located inside the trapping tube.
Figure 17:
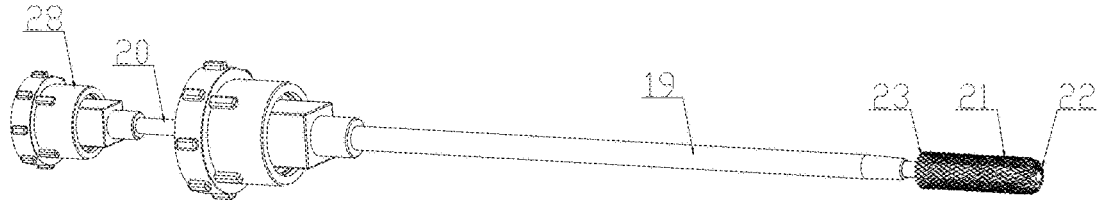
FIG. 17 is a schematic diagram of a structure of the thrombus trapping device of the trapping net located outside the trapping tube but not sleeved on the sheath tube.

As shown in FIGS. 14-17, the thrombus trapping device 200 includes the sheath tube 19, a trapping tube 20 and a trapping net 21 that can be accommodated inside the sheath tube 19, where a part of the sheath tube 19 is inserted into the blood vessel 300, while the other part of the sheath tube 19 is exposed to the blood vessel 300. The thrombectomy device 100, by means of the sheath tube 19, intervenes into the blood vessel 300 to extract the thrombus. The sheath tube 19, the trapping tube 20, the thrombectomy tube 1, the pushing tube 2, and the action tube 3 are coaxially arranged, and the trapping net 21 has the radial contraction state and the radial expansion state. As shown in FIG. 16, when the trapping net 21 is located inside the sheath tube 19, it is in a contracted state, and as shown in FIG. 17, when the trapping net 21 is located outside the sheath tube 19, it is in an expansion state. The trapping net 21 is provided with a first open end 22 and a second open end 23 that are axially opposite to each other, where the first open end 22 is connected to the distal end of the trapping tube 20. The trapping net 21 is configured to at least partially wrap the thrombectomy net 4 in the process that the thrombectomy net 4 with the embedded thrombus is withdrawn back into the thrombus trapping device 200 (namely the sheath tube 19). Specifically, the trapping net 21 wraps at least part of the first thrombectomy subnet 8 of the thrombectomy net 4, that is, it is capable to completely wrap the proximal end of the first thrombectomy subnet 8, because the proximal end of the first thrombectomy subnet 8 is an open end and net holes of the first thrombectomy subnet 8 are larger than those of the second thrombectomy subnet 9. Therefore, when the first thrombectomy subnet 8 is withdrawn back into the sheath tube 19, the thrombus easily escapes from the first thrombectomy subnet 8 due to the compression between the first thrombectomy subnet 8 and the inner wall of the sheath tube 19. However, this problem is solved effectively because the trapping net 21 at least partially wraps and fits the first thrombectomy subnet 8. To improve the effect, the net holes of the trapping net 21 can be configured to be smaller than those of the first thrombectomy subnet 8.

In an initial state, the trapping net 21 is turned over from inside to outside to form an outward flipping state, the first open end 22 is flipped inward and relatively fixedly connected to a distal end of the trapping tube 20 to form the distal end of the trapping net 21, and an inward flipping guide surface 24 is formed at a location near the first open end 22 of the trapping net 21. The inward flipping guide surface 24 is a tapered arc surface, which facilitates the withdrawal of the proximal end of the first thrombectomy subnet 8 to back into the sheath tube 19, and also facilitates the rapid inward flipping of inside of an outer part of the trapping net 21 to restore. The second open end 23 is a free end and formed as the proximal end of the trapping net 21. When the trapping tube 20 is configured to move from the distal end to the proximal end, the inside of an outer part of the trapping net 21 is quickly flipped inward along the inward flipping guide surface 24 to at least partially wrap the thrombectomy device 100. After the trapping net 21 is flipped inward in place, the first open end 22 is formed as the proximal end of the trapping net 21, and the second open end 23 is formed as the distal end of the trapping net 21. In the initial state, the trapping net 21 is in an outward flipping state and the inward flipping guide surface 24 is formed, so that the trapping net 21 is more likely to flip inward to restore, and the trapping net 21 is easily flipped to at least partially wrap the thrombectomy device 100. The wrapping is smoother and more stable, without the possibility of wrapping failure, so that it is effective to prevent the thrombus from escaping from the thrombectomy device 100 and capture the thrombus.

Moreover, the radial size of the trapping net 21 in the expansion rate is larger than the radial size of the sheath tube 19, so that when the trapping net 21 is located outside the sheath tube 19 and the trapping net 20 moves from the distal end to the proximal end, the trapping net 21 is gradually sleeved on the outer wall of the sheath tube 19 located inside the blood vessel 300 along the distal end of the sheath tube 19, so that the sheath tube 19 is capable to abut against the trapping net 21 to make the trapping net 21 flip inward, further resulting in that the trapping net 21 is more likely to flip inward, and the thrombectomy device 100 is wrapped more smoothly.

The sheath tube 19 is capable to abut against the trapping net 21 to make the trapping net 21 flip inward. It can be understood that, as shown in FIGS. 14-15, after the trapping net 21 is sleeved on the outer wall of the sheath tube 19, when the trapping tube 20 moves from the distal end to the proximal end, the distal end of the sheath tube 19 abuts against the first open end 22 of the trapping net 21 to make the trapping net 21 to flip inward. Alternatively, as shown in FIG. 17, the trapping net 21 is not sleeved on the outer wall of the sheath tube 19, and the second open end 23 of the trapping net 21 is capable to abut against the sheath tube 19, so that the distal end of the sheath tube 19 abuts against the second open end 23 of the trapping net 21 to make the trapping net 21 to flip inward. In other words, when the trapping tube 20 moves from the distal end to the proximal end, the second open end 23 of the trapping net 21 abuts against the distal end of the sheath tube 19, so that the trapping net 21 is not immediately sleeved on the outer wall of the sheath tube 19. At this time, the trapping net 21 flips inward because its second open end 23 abuts against the distal end of the sheath tube 19. Of course, it is also possible that after the second open end 23 of the trapping net 21 abuts against the distal end of the sheath tube 19, the trapping net 21 is gradually sleeved on the outer wall of the sheath tube 19 along the distal end of the sheath tube 19, as shown in FIG. 14, thus enabling the trapping net 21 to flip inward when the distal end of the sheath tube 19 abuts against the first open end 22 of the trapping net 21. In order to facilitate the smooth sleeving of the trapping net 21 at the distal end of the sheath tube 19, the distal end of the sheath tube 19 is configured to be a tapered end, so that the trapping net 21 is sleeved on the outer wall of the sheath tube 19 along the tapered end.

The trapping tube 20 includes an outer layer 25, an elastic net 26, and an inner layer 27, where the outer layer 25, the elastic net 26, and the inner layer 27 are coaxially arranged, and the elastic net 26 is located between the outer layer 25 and the inner layer 27, that is, the trapping tube 20 is of a three-layer tube structure. The elastic net 26 is mainly configured to improve the support strength, fracture and bending resistance, and tensile properties of the trapping tube 20. The first open end 22 of the trapping net 21 is fixedly connected to the distal end of the elastic net 26, which improves the connection strength between the trapping net 21 and the trapping tube 20. Of course, the distal end of the elastic net 26 may flip outward after extending out of the distal end of the trapping tube 20 to form the trapping net 21, so that the trapping net 21 easily flips inward to restore.

Figure 18:
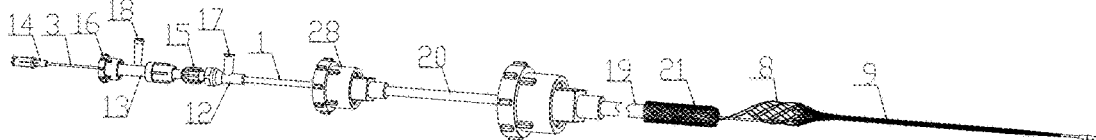
FIGS. 18-19 are state diagrams of FIG. 1.
Figure 19:
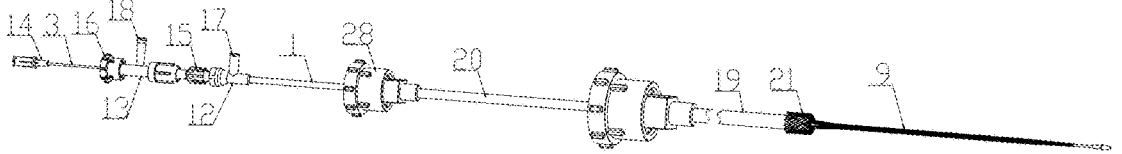

In actual use, after the thrombectomy device 100 captures a thrombus, the thrombectomy device 100 moves to the first open end 22 of the trapping net 21 from the distal end to the proximal end. After the first thrombectomy subnet 8 and the second thrombectomy subnet 9 are in a radial contraction state, as shown in FIG. 18, the trapping tube 20 and the thrombectomy tube 1 are relatively fixedly connected by means of the trapping tube base 28 at the proximal end of the trapping tube 20. For example, the trapping tube base 28 is rotated to fix, and then the trapping tube 20 is pulled by the sheath tube 19 from the distal end to the proximal end, so that the trapping tube 20, the thrombectomy tube 1, the pushing tube 2, and the action tube 3 are moved synchronously from the distal end to the proximal end, and the inside of an outer part of the trapping net 21 is quickly flipped inward along the inward flipping guide surface 24 to at least partially wrap the first thrombectomy subnet 8 of the thrombectomy net 4 and withdraw the first thrombectomy subnet 8 back into the sheath tube 19 together with the thrombectomy net 4, as shown in FIG. 19. Finally, the trapping tube 20 is further pulled by the sheath tube 19 from the distal end to the proximal end to withdraw the thrombectomy device 100 from the vessel 300, or withdraw from the vessel 300 together with the sheath tube 19 and the thrombectomy device 100. In an aspect, after the completion of thrombectomy through the thrombectomy net 4 and before the trapping net 21 wraps at least part of the thrombectomy net 4, the thrombectomy net 4 is configured to be in a contracted state overall at least in a stage, so that during the overall contraction process of the thrombectomy net 4, the thrombus in the thrombectomy net 4 is radially compressed to cause axial displacement, ultimately resulting in that distribution of the thrombi in the thrombectomy net 4 is relatively uniform, so that the radial size thereof will not be enlarged due to aggregation of a large amount of thrombi at a certain location of the thrombectomy net 4, and the thrombus will not be squeezed out of and escape due to collision between the thrombectomy net 4 and the inner wall of the sheath tube 19; in a further aspect, the trapping net 21 is flipped to at least partially fit the thrombectomy net 4 in the wrapped and contracted state, so that the thrombectomy net 4 can be withdrawn back into the sheath tube 19 in the wrapping process, thereby effectively avoiding the phenomenon of thrombus escaping when the thrombectomy net 4 with the embedded thrombus is withdrawn back into aspect, the aspect, the sheath tube 19, and moreover, the trapping net 21 in the outward flipping state is quickly flipped inward along the inward flipping guide surface 24 to at least partially wrap the thrombectomy net 4, so that the trapping net 21 is easily flipped to wrap at least part of the thrombectomy net 4, and the wrapping is smoother and more stable, without the possibility of wrapping failure.

It can be understood that although the present disclosure has been disclosed above with preferred embodiments, the above embodiments are not intended to limit the present disclosure. Any person skilled in the art, without departing from the scope of the technical solution of the present invention, may make many possible changes and modifications to the technical solution of the present disclosure by using the above disclosed methods and technical contents, or modify the technical solution of the present disclosure into equivalent embodiments with equivalent changes. Therefore, any simple alteration, equivalent change and modification which are made to the above embodiments in accordance with the technical essence of the present invention without departing from the contents of the technical solutions of the present invention all fall within the scope of protection of the technical solution of the present invention.

The invention claimed is:

1. A thrombectomy system, comprising a thrombectomy device (100), and a thrombus trapping device (200), the thrombectomy device (100) comprises a thrombectomy net (4), and a pushing tube (2), the pushing tube (2) is connected with the thrombectomy net (4), the thrombus trapping device (200) comprises a sheath tube (19), a trapping tube (20) and a trapping net (21) that can be stored in the sheath tube (19), both the trapping net (21) and the thrombectomy net (4) have a radial contraction state and a radial expansion state, the trapping net (21) is fixedly connected to the trapping tube (20), the pushing tube (2) is configured to push the thrombectomy net (4) into the blood vessel for thrombectomy and to withdraw the thrombectomy net (4) with an embedded thrombus back into the sheath tube (19), and the trapping net (21) is configured to at least partially wrap the thrombectomy net (4) in the process that the thrombectomy net (4) with the embedded thrombus is withdrawn back into the sheath tube (19), after completion of the thrombectomy through the thrombectomy net (4) and before the trapping net (21) wraps at least part of the thrombectomy net (4), the entire thrombectomy net (4) is in a contracted state at least in a stage, and the trapping net (21) is turned over from inside to outside to form an outward flipping state, with an inward flipping guide surface (24), when the trapping tube (20) and the pushing tube (2) are moved synchronously from the distal end to the proximal end, the sheath tube (19) abuts against the trapping net (21) to make the trapping net (21) flip inward, exposed inside of the trapping net (21) is quickly flipped inward along the inward flipping guide surface (24) to at least partially wrap the thrombectomy net (4), and is withdrawn back into the sheath tube (19) together with the thrombectomy net (4);

the thrombectomy device (100) further includes an action tube (3), the action tube (3) is at least partially and slidably arranged in the pushing tube (2), the action tube (3) is provided with a first action block (5) and a second action block (6) that are both fixed on the action tube and spaced apart from each other, a distal end of the thrombectomy net (4) is fixedly connected to a sliding block (7) and converged at the sliding block (7) to form a retraction end, the sliding block (7) is sleeved on the action tube (3) and configured to slide within a limited range of distance between the first action block (5) and the second action block (6), the first action block (5) is located inside the thrombectomy net (4), the second action block (6) is located outside the thrombectomy net (4), when relative displacement against the pushing tube (2) occurs after the action tube (3) is pushed from the proximal end to the distal end, the action tube (3) can drive the sliding block (7) to slide toward the distal end direction through the first action block (5) so that the thrombectomy net (4) elongates to radially contract, when relative displacement against the pushing tube (2) occurs after the action tube (3) is pulled from the distal end to the proximal end, the action tube (3) can drive the sliding block (7) to slide toward the proximal end direction through the second action block (6) so that the thrombectomy net (4) shortens to radially expand.

2. The thrombectomy system according to claim 1, wherein the thrombectomy net (4) comprises a first thrombectomy subnet (8) and a second thrombectomy subnet (9) connected in sequence, the first thrombectomy subnet (8) is configured for separating a thrombus from a blood vessel by cutting the thrombus therein, and the second thrombectomy subnet (9) is configured for collecting the thrombus separated out, the trapping net (21) is configured to at least partially wrap the first thrombectomy subnet (8).

3. The thrombectomy system according to claim 2, wherein when relative displacement against the pushing tube (2) occurs after the action tube (3) is configured to move in a predetermined direction, the first thrombectomy subnet (8) and the second thrombectomy subnet (9) are driven to radially contract or to radially expand.

4. The thrombectomy system according to claim 3, wherein the action tube (3), the pushing tube (2), the trapping tube (20), and the sheath tube (19) are coaxially arranged.

5. The thrombectomy system according to claim 3, wherein a distal end of the second thrombectomy subnet (9) is sleeved on the action tube (3) and is capable to slide within a limited range of distance between the first action block (5) and the second action block (6), a proximal end of the first thrombectomy subnet (8) is fixedly connected to a distal end of the pushing tube (2).

6. The thrombectomy system according to claim 5, wherein relative displacement against the pushing tube (2) occurs after the action tube (3) is pushed from the proximal end to the distal end, the pushing tube (2), by means of the first action block (5), is capable to drive the first thrombectomy subnet (8) and the second thrombectomy subnet (9) to radially contract; the first action block (5) is an annular boss protruding from the outer surface of the action tube (3), used for supporting the thrombectomy net (4) to ensure that the thrombectomy net (4) still has a certain thrombus storage space when in the radially contracted state.

7. The thrombectomy system according to claim 5, wherein relative displacement against the pushing tube (2) occurs after the action tube (3) is pulled from the distal end to the proximal end, the action tube (3), by means of the second action block (6), is capable to drive the first thrombectomy subnet (8) and the second thrombectomy subnet (9) to radially expand.

8. The thrombectomy system according to claim 2, wherein the trapping net (21) is provided with a first open end (22) and a second open end (23) that are axially opposite to each other, before the trapping net (21) wraps at least part of the first thrombectomy subnet (8), the first open end (22) is flipped inward and relatively fixedly connected to a distal end of the trapping tube (20) to form the distal end of the trapping net (21), and the second open end (23) is a free end and is formed as a proximal end of the trapping net (21).

9. The thrombectomy system according to claim 8, wherein the inward flipping guide surface (24) is formed at a location near the first open end (22) of the trapping net (21); the trapping tube (20) includes an outer layer (25), an elastic net (26), and an inner layer (27) coaxially arranged, with the elastic net (26) positioned between the outer layer (25) and the inner layer (27); a distal end of the elastic net (26) is fixedly connected to the first open end (22) of the trapping net (21), or a distal end of the elastic net (26) extends beyond the distal end of the trapping tube (20) and then flips outward to form the trapping net (21).

10. The thrombectomy system according to claim 8, wherein when the trapping tube (20) and the pushing tube (2) are moved synchronously from the distal end to the proximal end, and after the trapping net (21) is flipped inward in place, the first open end (22) is formed as the proximal end of the trapping net (21), and the second open end (23) is formed as the distal end of the trapping net (21).

* * * * *